(12) United States Patent
Forouhi et al.

(10) Patent No.: US 6,710,865 B2
(45) Date of Patent: Mar. 23, 2004

(54) METHOD OF INFERRING OPTICAL PARAMETERS OUTSIDE OF A MEASUREMENT SPECTRAL RANGE

(75) Inventors: Abdul Rahim Forouhi, Cupertino, CA (US); Dale A. Harrison, Tracy, CA (US); Erik Maiken, Santa Clara, CA (US); John C. Lam, San Jose, CA (US)

(73) Assignee: N&K Technology, Inc., Santa Clara, CA (US)

( * ) Notice: Subject to any disclaimer, the term of this patent is extended or adjusted under 35 U.S.C. 154(b) by 157 days.

(21) Appl. No.: 09/953,578

(22) Filed: Sep. 14, 2001

(65) Prior Publication Data

US 2002/0113957 A1 Aug. 22, 2002

(Under 37 CFR 1.47)

Related U.S. Application Data

(60) Provisional application No. 60/232,667, filed on Sep. 14, 2000.

(51) Int. Cl.[7] .......................... G01N 21/41; G01N 21/43
(52) U.S. Cl. ........................................ 356/128; 356/517
(58) Field of Search .......................... 356/73, 630, 128, 356/517; 250/559.28, 559.39

(56) References Cited

U.S. PATENT DOCUMENTS

| 4,162,208 | A | * | 7/1979 | Aladjem et al. | 436/514 |
|---|---|---|---|---|---|
| 4,488,245 | A | * | 12/1984 | Dalke et al. | 382/167 |
| 4,905,170 | A | * | 2/1990 | Forouhi et al. | 356/631 |
| 6,091,485 | A | * | 7/2000 | Li et al. | 356/73 |
| 6,115,528 | A | * | 9/2000 | Schmucker et al. | 385/138 |
| 6,222,199 | B1 | * | 4/2001 | Freeouf | 250/559.27 |
| 6,320,179 | B1 | * | 11/2001 | Cox et al. | 250/214 A |
| 6,392,756 | B1 | * | 5/2002 | Li et al. | 356/632 |
| 6,556,306 | B2 | * | 4/2003 | Jiang et al. | 356/517 |

OTHER PUBLICATIONS

Lide, David R. (Editor), CRC Handbook of Chemistry and Physics, 1993, CRC press, 74th edition, (12) 109–113.*

* cited by examiner

Primary Examiner—Russell Adams
Assistant Examiner—Andrew Sever
(74) Attorney, Agent, or Firm—Lumen Intellectual Property Services, Inc.

(57) ABSTRACT

The present invention provides a method for inferring optical parameters of a sample in a predictive spectral range by use of the known values of the optical parameters in a predetermined measurement spectral range. The method of the present invention capitalizes on the Forouhi-Bloomer dispersion equations for the optical constants n and k.

18 Claims, 2 Drawing Sheets

METHOD OF INFERRING OPTICAL PARAMETERS OUTSIDE OF A MEASUREMENT SPECTRAL RANGE

CROSS-REFERENCE TO RELATED APPLICATIONS

This application is cross-referenced to and claims priority from U.S. Provisional application 60/232,667 filed Sep. 14, 2000, which is hereby incorporated by reference.

FIELD OF THE INVENTION

This invention relates to optical metrology of materials. More specifically, it provides a novel method for inferring optical properties in spectral ranges that may not be readily accessible experimentally.

BACKGROUND

Thin-film fabrication & characterization have become an indispensable part of modern technology. Practical applications increasingly demand that the characterization of the fabricated films be carried out in a convenient, accurate, real-time, and customized fashion.

Among the physical characteristics that are of practical importance are the optical properties of materials. Such properties are not only of fundamental and practical significance in their own rights, they are also intimately related to other physical characteristics, such as electrical properties. A method that has proved to be particularly effective in characterizing the optical properties of thin films is the so-called "n&k" method. This is a measurement technique that simultaneously determines the thickness d, spectra of physical constants—namely, index of refraction n and extinction coefficient k, energy band-gap $E_g$, and interface roughness $\sigma$ of thin films deposited on opague or transparent substrates. At the core of the "n&k" method are the original Forouhi-Bloomer dispersion equations for n and k, as described in U.S. Pat. No. 4,905,170. It is applicable to a broad range of semiconductor, dielectric and thin metal films, and is valid from the vacuum-ultra-violet (VUV) to the near-infra-red (NIR) range in spectrum. The "n&k" method has been widely used in the spectrum range extending from 190 to 1000 nm, yielding a great deal of information about the optical and dielectric properties of various think-film materials.

The optical properties in the spectrum ranges below 190 nm and above 1000 nm are also of considerable interest. However, the body of the data in these spectral ranges is strikingly sparse, relative to what is available in the DUV, visible and NIR ranges. This is largely due to the fact that the measurement instrument in these "extreme" spectral ranges is yet to be readily available, owing to various experimental limitations. Therefore, it would be very useful to extend the "n&k" method to these extreme spectral ranges, without the need of carrying out the actual measurements.

OBJECTS AND ADVANTAGES

Accordingly it is a principal object of the present invention to provide a method for inferring optical parameters of a sample in a predictive spectral range that may not be readily accessible experimentally. The method of the present invention utilizes the measurements of the optical parameters in a predetermined spectral range where the optical parameters can be determined with sufficient details, to extract the information about the parameters in the predictive spectral range.

These and other objects and advantages will become apparent from the following description and accompanying drawings.

SUMMARY OF THE INVENTION

The present invention provides a method for inferring optical parameters of a sample in a predictive spectral range by using the known values of the optical parameters in a predetermined measurement spectral range. The method of the present invention capitalizes on the Forouhi-Bloomer dispersion equations for the optical constants n and k.

More specifically, the inventive method utilizes the "n&k" method to obtain the "measured" values of n and k as functions of wavelength $\lambda$ respectively in a predetermined measurement spectral range. The measurements are carried out at a resolution of $\lambda$ that is sufficing to bring out the details of n and k spectra. It then constructs the analytical expressions for n=n(E) and k=k(E) in a predictive spectral range by use of the Forouhi-Bloomer dispersion equations for n and k, until the "inferred" values of n and k given by the constructed analytical expressions agree with the "measured" values obtained from the experimental measurements. The thus constructed analytical expressions n=n(E) and k=k(E) can be subsequently used to provide the optical constants in the predictive spectral range.

The method of the present invention can be applied to a variety of applications in which it is desirable to obtain the optical properties of a sample in a particular spectral range that may not be readily accessible experimentally. It can also be utilized in situations where a quick and reliable estimation of various optical properties is needed, before carrying out laborious experimentation.

As a way of demonstrating the utility of the present invention, the inventive method can be used to deduce the dielectric constant $\kappa$ of a material, thereby averting experimental measurements of capacitance (or other physical parameters) that have been conventionally used to determine $\kappa$.

The novel features of this invention, as well as the invention itself, will be best understood from the following drawings and detailed description.

DETAILED DESCRIPTION

Figure 1:
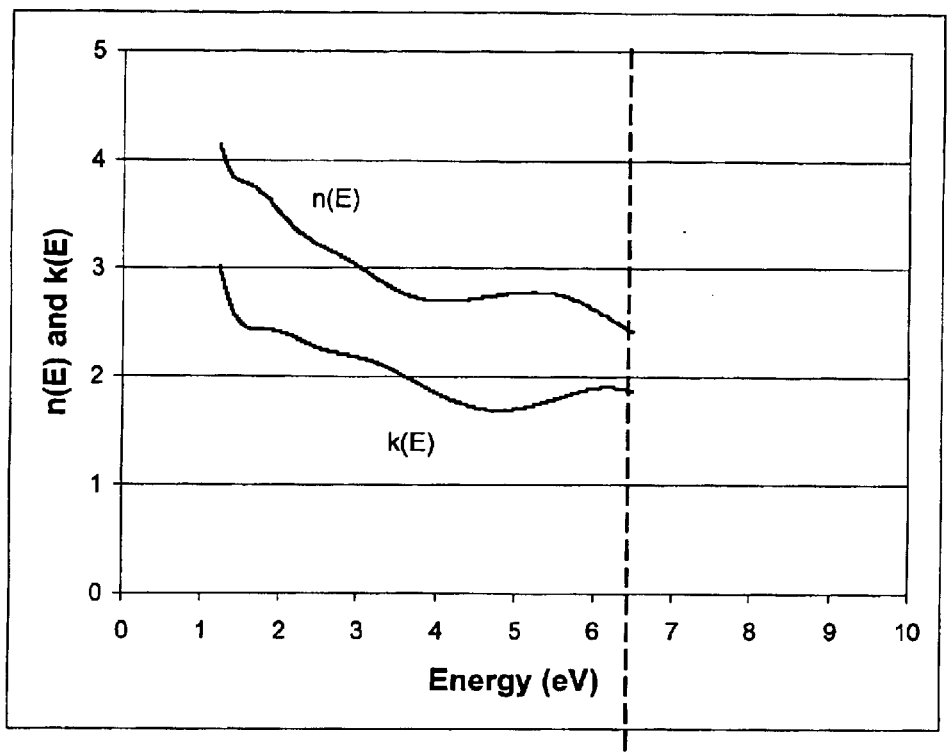
FIG. 1 provides an illustrative depiction of the "measured" index of refraction n and extinction coefficient k as a function of energy E in an exemplary measurement spectral range.

Although the following detailed description contains many specific details for the purposes of illustration, anyone of ordinary skill in the art will appreciate that many variations and alterations to the following details are within the scope of the invention. Accordingly, the exemplary embodiment of the invention described below is set forth without any loss of generality to, and without imposing limitations upon, the claimed invention.

For the purpose of elucidating the principle of the present invention, the underlying principle of the "n&k" method is briefly described below. A more detailed description is provided in U.S. Pat. No. 4,905,170, which is incorporated herein by reference for all purposes.

Both n and k are functions of wavelength $\lambda$, i.e., $n=n(\lambda)$ and $k=k(\lambda)$. Since $\lambda$ is related to photon energy E, according to $E=hc/\lambda$ (where h is Planck's constant and c is the speed of light in vacuum), n and k can also be described as functions of photon energy E, i.e., $n=n(E)$ and $k=k(E)$. The underpinning factor that relates $n=n(E)$ to $k=k(E)$ is the Kramers-Kronig dispersion relation, which dictates that $n=n(E)$ be determined as the Hilbert transformation of $k=k(E)$. Hence, a viable description of $n=n(E)$ and $k=k(E)$ should be consistent with the Kramers-Kronig dispersion relation.

For a pure crystalline material, $n=n(\lambda)$ and $k=k(\lambda)$ are distinct quantities, characteristic of the chemical elements comprising the crystal. For a thin film, however, $n=n(\lambda)$ and $k=k(\lambda)$ may depend significantly on the manufacture process. If these conditions vary during thin film deposition, the microstructure and composition of the film will change accordingly. In many cases, these changes may manifest themselves as changes in the optical properties of the fabricated materials.

In practice, $n=n(\lambda)$ and $k=k(\lambda)$ spectra cannot be directly measured. Rather, they are discursively determined from measurements of optical quantities, such as reflectance R and transmittance T. U.S. Pat. No. 4,905,170 by Forouhi and Bloomer discloses a method for determining these spectra from the reflectance spectrum of a thin film. Their method centers on a formulation for the optical constants $n=n(E)$ and $k=k(E)$, which has been termed as the Forouhi-Bloomer dispersion equations in the art, as shown below:

$$k(E) = \sum_{i=1}^{q} \frac{A_i(E-E_g)^2}{E^2 - B_i E + C_i} \quad (1)$$

$$n(E) = n(\infty) + \sum_{i=1}^{q} \frac{B_{oi} E + C_{oi}}{E^2 - B_i E + C_i} \quad (2)$$

In the above equations, the integer q specifies the number of terms involved in the respective sums. Each term in the sum for $n=n(E)$ and for $k=k(E)$ contributes either a peak or a shoulder in their respective spectra. The first term (q=1) describes the spectra of an amorphous material. Polycrystalline or crystalline materials are represented by higher order terms. $E_g$ represents the optical energy band-gap. The parameters $A_i$, $B_i$, and $C_i$ are directly related to the electronic configuration of the material. The parameter $n(\infty)$ represents the lim of $n=n(E)$ as $E\to\infty$ (or $\lambda\to 0$). The parameters $B_{oi}$ and $C_{oi}$ are functions of $A_i$, $B_i$, $C_i$, and $E_g$. Note that Eq. (2) for $n=n(E)$ is derived from Eq. (1) for $k=k(E)$ by way of the Kramers-Kronig dispersion relation.

The above equations are further combined with a parameterized model for interface roughness and incorporated into the Fresnel coefficients to generate algorithms that describe the theoretical reflectance R and transmittance T of single or multi-layer films. By comparing measurements of R and T with the theoretical predictions, by use of a least squares fitting routine, $n=n(\lambda)$ and $k=k(\lambda)$ spectra, film thickness d, energy band-gap $E_g$, and interface roughness $\sigma$ can be determined. This essentially constitutes the "n&k" method.

As described above, the "n&k" method has been widely used in the spectral range of 190–1000 nm, yielding a great deal of information about the optical properties of a variety of thin-film materials. The lack of the experimental data on various optical properties in the spectral ranges below 190 nm and above 1000 nm respectively is due to the experimental limitations, though the Forouhi-Bloomer dispersion equations are in principle valid over a wide range of photon energies covering a substantial portion of the entire spectrum of electromagnetic radiation.

Figure 2:
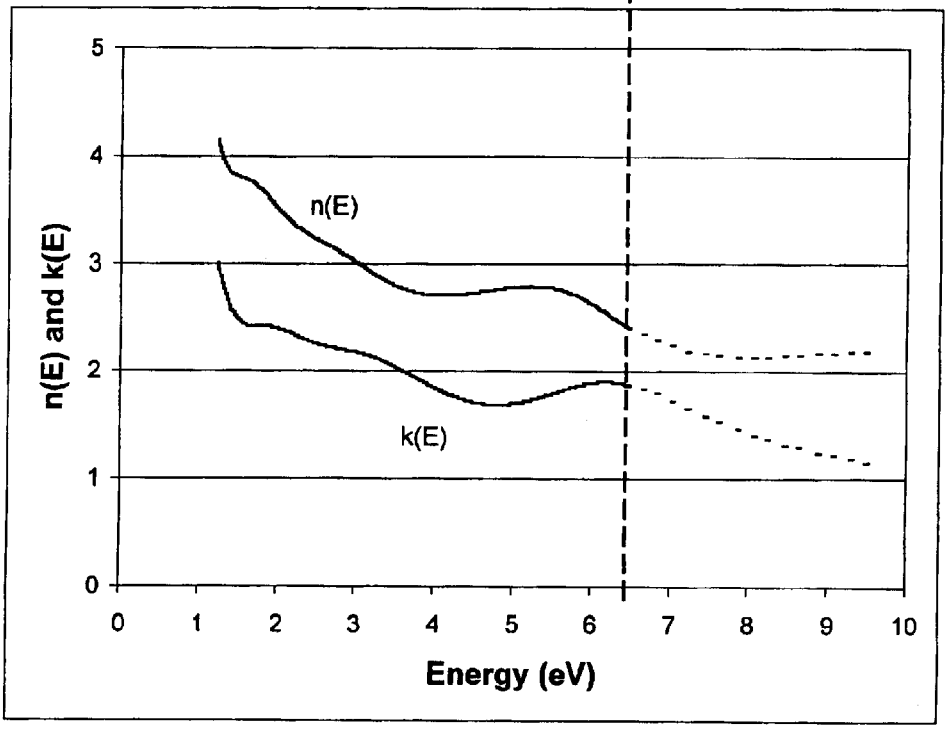
FIG. 2 provides an illustrative depiction of the "inferred" index of refraction n and extinction coefficient k as a function of energy E in an exemplary predictive spectral range according to the present invention, along with the spectrum of the "measured" n and k in the measurement spectral range shown in FIG. 1.
Figure 3:
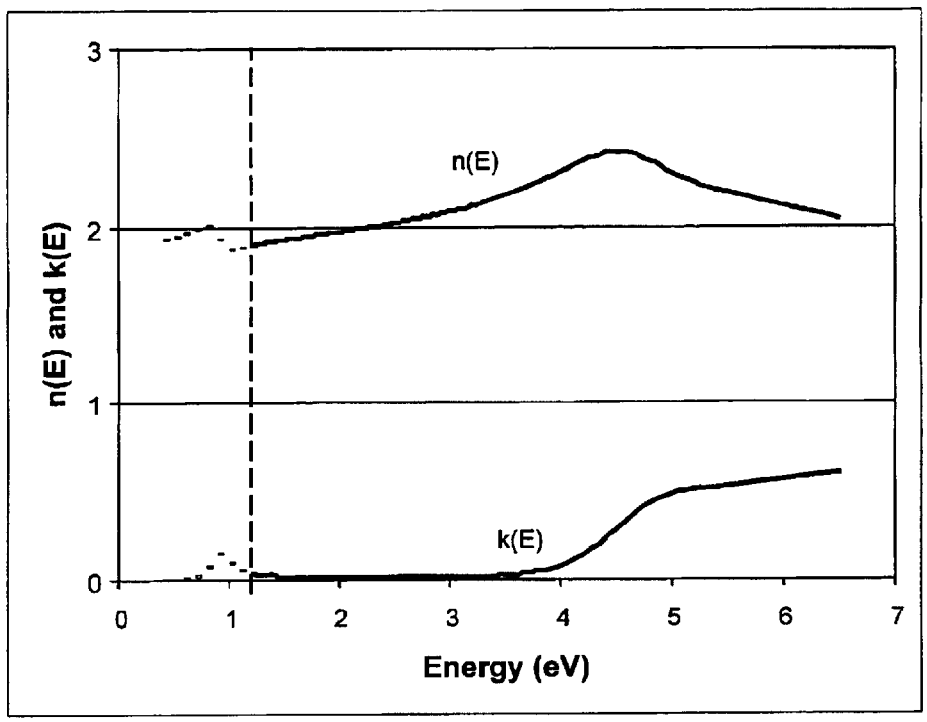
FIG. 3 provides an illustrative depiction of the "inferred" index of refraction n and extinction coefficient k as a function of energy E in an exemplary predictive spectral range according to the present invention, along with the spectrum of the "measured" n and k.

In view of the forgoing, the present invention provides a method for inferring the optical properties of a sample without the need of carrying out the actual measurements. The inventive method utilizes the "n&k" method outlined above to obtain the "measured" values of n and k as functions of wavelength $\lambda$ respectively in a predetermined measurement spectral range. The measurements should be carried out at a resolution of $\lambda$ that is sufficient to bring out the details of n and k spectra. By way of example, FIG. 1 provides an illustrative depiction of the "measured" n and k as a function of energy E in an exemplary measurement spectral range, extending from 1.24 eV (1000 nm) to 6.53 eV (190 nm). (Note: in this spectral range, the measurements are typically carried out at an increment of $\lambda$ about 1 nm.) The inventive method then constructs the analytical expressions for $n=n(E)$ and $k=k(E)$ by incrementally carrying out more terms in the sums of Eqs. (1) and (2), until the "inferred" values of n and k given by the constructed analytical expressions agree with the "measured" values obtained from the experimental measurements. As a way of example, FIG. 2 provides an illustrative depiction of the "inferred" n and k as a function of energy E in an exemplary predictive spectral range extending above 6.53 eV (below 190 nm), along with the "measured" n and k in the measurement spectral range shown in FIG. 1. Similarly as a way of example, FIG. 3 provides an illustrative depiction of the "inferred" n and k as a function of energy E in an exemplary predictive spectral range extending below 1.24 eV (above 1000 nm), along with the "measured" n and k in the measurement spectral range. The thus constructed analytical expressions $n=n(E)$ and $k=k(E)$ can be subsequently used to provide the optical constants in other spectral regions of interest.

Those skilled in the art will recognize that the underlying mechanism of the inventive method described above hinges on the fundamental Kramers-Kronig dispersion relation, which dictates that the value of $n=n(E)$ (or $k=k(E)$) at a particular value of E be related to $n=n(E)$ (or $k=k(E)$) at other values of E.

As such, the method of the present invention can be applied to a variety of applications in which optical properties in a particular spectral range that may not be readily accessible experimentally are needed. It can also be utilized in situations where a quick and reliable estimation of various optical properties is desired, before carrying out laborious experimentation.

As a way of illustrating the utility of the present invention, the method of the present invention can be used to deduce the dielectric constant $\kappa$ of a material. This is based on that the complex dielectric function $\epsilon$ is given by, $$\epsilon = \epsilon_1 - i\epsilon_2 \quad (3)$$

where the real part $\epsilon_1$ and the imaginary part $\epsilon_2$ of $\epsilon$ are generally functions of wavelength $\lambda$ (or frequency $\omega$—as conventionally expressed). The complex index of refraction can be expressed as, $$N = n - ik \tag{4}$$

Since $\epsilon = N^2$, it follows that $$\epsilon_1 = n^2 - k^2 \tag{5}$$

and $$\epsilon_2 = 2nk \tag{6}$$

Given that the dielectric constant, $$\kappa = \lim_{\lambda \to \infty} \varepsilon_1 \tag{7}$$

thus, $$\kappa \propto [n(\lambda \to \infty)]^2 \tag{8}$$

Figure 4:
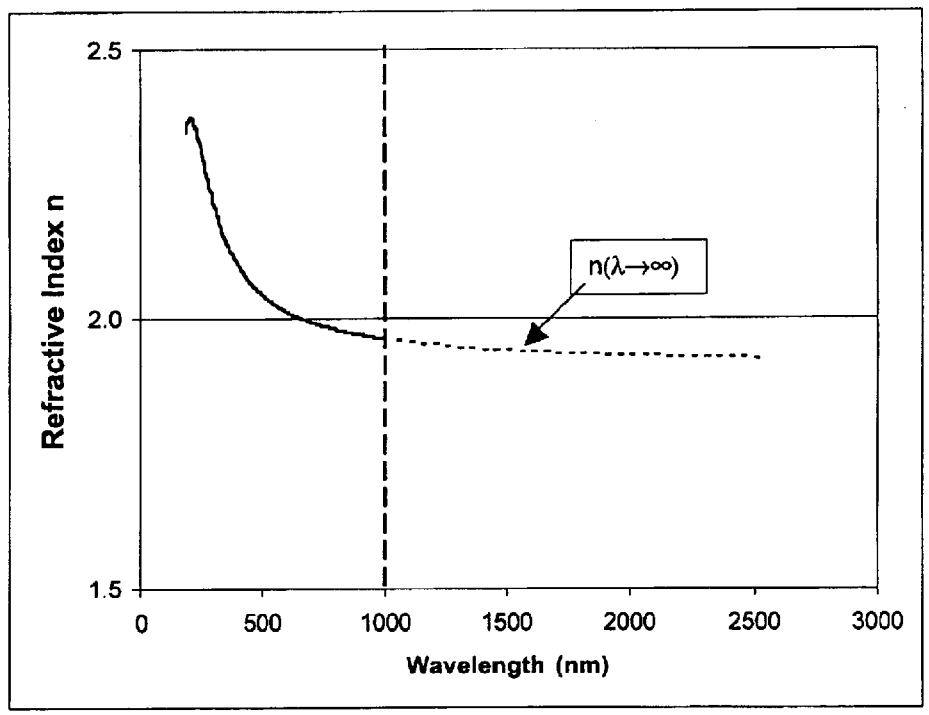
FIG. 4 provides an exemplary depiction of asymptotic behavior of index of refraction n at large wavelength $\lambda$.

That is, if the asymptotic behavior of n at large wavelength λ is known, the dielectric constant κ can be accordingly determined. FIG. 4 shows an exemplary depiction of the asymptotic behavior of index of refraction n at large wavelength λ. Hence, by applying the method of the present invention as described above to infer the index of refraction of n of a sample in the large-λ spectral range (e.g., above 1000 nm), the dielectric constant κ of the sample can be deduced. This has an advantage of averting experimental measurements of capacitance (or other physical parameters) of the sample, which have been conventionally used to determine κ.

A skilled artisan will recognize that the above exemplary case provides only one of many utilities of the present invention. Those skilled in the art will know how to make use of the present invention for a given application.

Although the present invention and its advantages have been described by way of the above exemplary embodiments, it should be understood that various changes, substitutions, and alterations can be made herein without departing from the principle and the scope of the invention. Accordingly, the scope of the present invention should be determined by the following claims and their legal equivalents.

What is claimed is:

1. A method for inferring an optical parameter in a predictive spectral range outside of a measurement spectral range, comprising:
    a) obtaining "measured" values of said optical parameter in said measurement spectral range from 190 nm to 1000 nm at a wavelength resolution of about 1 nm;
    b) constructing an analytical expression for describing said optical parameter by use of a theoretical function, such that said analytical expression yields said "measured" values of said optical parameter in said measurement spectral range; and
    c) using said analytical expression to infer said optical parameter in said predictive spectral range.

2. The method of claim 1, wherein said optical parameter is an index of refraction of said sample.

3. The method of claim 2, wherein said step of obtaining is carried out by way of the "n&k" method.

4. The method of claim 2, wherein said theoretical function comprises the Forouhi-Bloomer dispersion equation for index of refraction.

5. The method of claim 2, wherein said predictive spectral range is above 1000 nm in wavelength.

6. The method of claim 5, wherein said index of refraction is used to determine a dielectric constant of said sample.

7. The method of claim 1, wherein said optical parameter is an extinction coefficient of said sample.

8. The method of claim 7, wherein said step of obtaining is carried out by way of the "n&k" method.

9. The method of claim 7, wherein said theoretical function comprises the Forouhi-Bloomer dispersion equation for extinction coefficient.

10. The method of claim 1, wherein said predictive spectral range is less than 190 nm in wavelength.

11. The method of claim 1, wherein said predictive spectral range is greater than 1000 nm in wavelength.

12. A method of using the n&k method for inferring an optical parameter in a predictive spectral range outside of a measurement spectral range, comprising:
    (a) obtaining "measured" values of said optical parameter in said measurement spectral range from 190 nm to 1000 nm at a wavelength resolution of about 1 nm;
    (b) constructing an analytical expression for describing said optical parameter by use of a theoretical function, such that said analytical expression yields said "measured" values of said optical parameter in said measurement spectral range; and
    (c) using said analytical expression to infer said optical parameter in said predictive spectral range.

13. The method of claim 12, wherein said optical parameter is an index of refraction of said sample.

14. The method of claim 13, wherein said predictive spectral range is above 1000 nm in wavelength.

15. The method of claim 14, wherein said index of refraction is used to determine a dielectric constant of said sample.

16. The method of claim 12, wherein said optical parameter is an extinction coefficient of said sample.

17. The method of claim 12, wherein said predictive spectral range is less than 190 nm in wavelength.

18. The method of claim 12, wherein said predictive spectral range is greater than 1000 nm in wavelength.

* * * * *